US011141400B2

(12) United States Patent
Dressman et al.

(10) Patent No.: US 11,141,400 B2
(45) Date of Patent: Oct. 12, 2021

(54) METHOD OF TREATMENT

(71) Applicant: Vanda Pharmaceuticals Inc., Washington, DC (US)

(72) Inventors: Marlene Michelle Dressman, Germantown, MD (US); Mihael H. Polymeropoulos, Potomac, MD (US); Paolo Baroldi, Potomac, MD (US)

(73) Assignee: Vanda Pharmaceuticals Inc., Washington, DC (US)

( * ) Notice: Subject to any disclaimer, the term of this patent is extended or adjusted under 35 U.S.C. 154(b) by 0 days.

(21) Appl. No.: 16/800,611

(22) Filed: Feb. 25, 2020

(65) Prior Publication Data

US 2020/0188346 A1 Jun. 18, 2020

Related U.S. Application Data

(63) Continuation of application No. 16/517,111, filed on Jul. 19, 2019, now Pat. No. 10,610,511, which is a continuation of application No. 14/511,669, filed on Oct. 10, 2014, now Pat. No. 10,376,487.

(60) Provisional application No. 61/903,354, filed on Nov. 12, 2013, provisional application No. 61/927,465, filed on Jan. 14, 2014.

(51) Int. Cl.
*A61K 31/343* (2006.01)

(52) U.S. Cl.
CPC .................. *A61K 31/343* (2013.01)

(58) Field of Classification Search
CPC ..... A61K 31/343; A61K 9/0053; A61P 43/00; A61P 25/20; A61P 25/00
USPC ........................................................ 514/469
See application file for complete search history.

(56) References Cited

U.S. PATENT DOCUMENTS

| 5,420,152 A | 5/1995 | Lewy et al. |
| 5,856,529 A | 1/1999 | Catt et al. |

(Continued)

FOREIGN PATENT DOCUMENTS

| JP | 2013163691 A | 8/2013 |
| WO | 2008011120 A1 | 1/2008 |
| WO | 2008011150 A1 | 1/2008 |

(Continued)

OTHER PUBLICATIONS

Keijzer et al., "Why the dim light melatonin onset (DLMO) should be measured before treatment of patients with circadian rhythm sleep disorders," Sleep Medicine Reviews,18 (2004) 333-339.

(Continued)

*Primary Examiner* — Taylor V Oh
(74) *Attorney, Agent, or Firm* — Hoffman Warnick LLC

(57) ABSTRACT

One embodiment of the invention provides a method for administering tasimelteon to a human patient that comprises orally administering an effective dose of tasimelteon under fasted conditions. Fasted conditions may comprise administering the tasimelteon without food, no food at least ½ hour prior to administration, no food at least 1 hour prior to administration, no food at least 1½ hours prior to administration, no food at least 2 hours prior to administration, no food at least 2½ hours prior to administration, or no food at least 3 hours prior to administration. According to such embodiments, tasimelteon may be administered, for example, at a dose of 20 mg/d. Tasimelteon may be administered where, for example, the patient is being treated for a circadian rhythm disorder or for a sleep disorder, including, for example, Non-24 Disorder.

10 Claims, 1 Drawing Sheet

(56) References Cited

U.S. PATENT DOCUMENTS

2009/0105333 A1     4/2009    Birznieks et al.
2013/0197076 A1     8/2013    Dressman et al.

FOREIGN PATENT DOCUMENTS

WO      2008070795 A2    6/2008
WO      2013112949 A2    8/2013

OTHER PUBLICATIONS

Medicine and Drug Journal, 2001, 47(2), pp. 818-819.
Journal of Clinical Pharmacology, 2004, 44(10), pp. 1210, 105.
English Translation of Notice of Reasons for Rejection for Japanese Patent Application No. 2016-546950, dated Aug. 21, 2018, 4 pages.
Russian Office Action for Application No. 2016 133 348, dated Sep. 26, 2018, 12 pages.
Riviere K. et al., Clinical Pharmacology and Biopharmacology review(s), Apr. 12, 2014, c. 2-76, 27-22.
Rajaratnam et al. (Lancet, 373, 2009, 482-91).
Guidance for Industry (Food-Effect Bioavailability and Fed Bioequivalence Studies, 2002).
Zisapel (CNS Drugs, 15, 2001, 311-328).
Hardeland, "Tasimelteon, a melatonin agonist for the treatment of insomnia and circadian rhythm sleep disorders," Curr Opin Investig Drugs. 10(7):691-701 (2009).
International Search Report and Written Opinion for International Application No. PCT/US2015/010410, dated Mar. 24, 2015, (12 pages).
Rajaratnam et al. (Lancet, 373, 2009, 482-91) (Year: 2009).
Guidance for Industry (Food-Effect Bioavailability and Fed Bioequivalence Studies, 2002) (Year: 2002).
Office Action and English Translation thereof for corresponding JP Application No. 2016-546950 dated Sep. 23, 2020, 29 pages.
NEW Pharmacology, 1997, edited by Ryuichi Kato, published by Nankodo Co., Ltd., pp. 570-583 (newly cited document presenting common knowledge in the art), 14 pages.
New Pharmacology, 1997, edited by Ryuchi Kato, published by Nankodo Co., Ltd., pp. 13-34 (newly cited document presenting common knowledge in the art), 22 pages.
Slaine, "Calculating Urine PK Parameters," Dec. 6, 2012, pp. 1-5 (XP055754460), Retrieved from the Internet: URL:https://www.certara.com/knowledge-base/calculating-urine-pk-parameters/ [retrieved on Nov. 26, 2020].

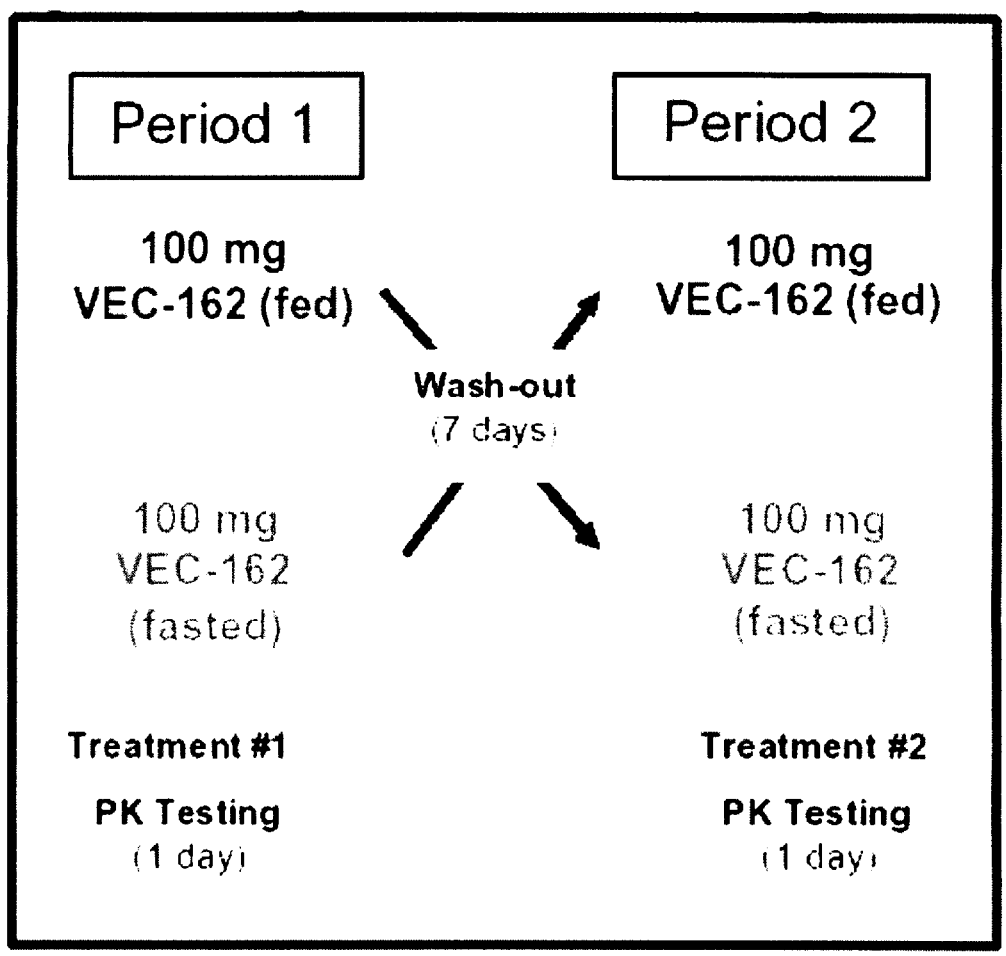

METHOD OF TREATMENT

CROSS-REFERENCE TO RELATED APPLICATIONS

This application is a continuation application of co-pending U.S. patent application Ser. No. 16/517,111, filed 19 Jul. 2019, which is a continuation of then-co-pending U.S. patent application Ser. No. 14/511,669, filed 10 Oct. 2014, now U.S. Pat. No. 10,376,487, which claims priority to U.S. Provisional Application Ser. No. 61/927,465, filed 14 Jan. 2014, and 61/903,354, filed 12 Nov. 2013, each of which is hereby incorporated herein as though fully set forth.

BACKGROUND OF THE INVENTION

Tasimelteon, and methods of using and processes for making tasimelteon, are disclosed in various references, including U.S. Pat. No. 5,856,529, US Patent Application Publication No. 20090105333, and US Patent Application Publication No. 20130197076, copies of which are appended hereto and are incorporated herein by reference as though fully set forth.

SUMMARY

One embodiment of the invention provides a method for administering tasimelteon to a human patient that comprises orally administering an effective dose of tasimelteon under fasted conditions. Fasted conditions may comprise administering the tasimelteon without food, no food at least ½ hour prior to administration, no food at least 1 hour prior to administration, no food at least 1½ hours prior to administration, no food at least 2 hours prior to administration, no food at least 2½ hours prior to administration, or no food at least 3 hours prior to administration. According to such embodiments, tasimelteon may be administered, for example, at a dose of 20 mg/d. Tasimelteon may be administered where, for example, the patient is being treated for a circadian rhythm disorder or for a sleep disorder, including, for example, Non-24 Disorder.

Another embodiment of the invention provides a method for administering tasimelteon to a human patient that comprises instructing the patient that tasimelteon should be taken without food.

Still another embodiment of the invention provides a method for shortening $T_{max}$ in a human patient being treated with tasimelteon, said method comprising orally administering an effective dose of tasimelteon under fasted conditions.

In still yet another embodiment, the invention provides a method of marketing or selling tasimelteon that comprises informing prescribers, patients, and/or insurers that tasimelteon should be taken under fasted conditions, such as by including such instructions in printed prescribing information that is packaged with a container comprising tasimelteon capsules.

BRIEF DESCRIPTION OF THE DRAWINGS

These and other features of this invention will be more readily understood from the following detailed description of the various aspects of the invention taken in conjunction with the accompanying drawings that depict various embodiments of the invention, in which:

FIG. 1 shows a flow diagram of a study related to the invention.

It is noted that the drawings of the invention are not to scale. The drawings are intended to depict only typical aspects of the invention, and therefore should not be considered as limiting the scope of the invention.

DESCRIPTION OF THE INVENTION

This invention relates to administration of tasimelteon under fasted conditions, i.e., without food.

A clinical study was undertaken to investigate the effects of food on administration of tasimelteon. Specifically, the primary objective of the study was to investigate the influence of food (high-calorie/high-fat) on the pharmacokinetics of 100 mg of tasimelteon in healthy subjects. This was a single-center, open-label, crossover design which lasted up to 5 weeks. 26 Healthy male and female subjects (18-50 years old) were enrolled in the study. There was a 2-period, randomized, 2-sequence crossover design where each subject received 100 mg tasimelteon either with or without food. Subjects were randomly assigned to receive a 100 mg tasimelteon capsule under fasted conditions or a 100 mg tasimelteon capsule under fed conditions (i.e., 30 minutes after beginning to ingest a high-fat meal). There was a 7-day washout between treatment groups. FIG. 1 depicts an example of the overall study design. In FIG. 1, tasimelteon is referred to as VEC-162.

For purposes of the study depicted in FIG. 1, administration under fasted conditions was administration with 240 mL of water at approximately 6:00 AM, after at least a 10-hour fast. Subjects were not allowed to eat any food for at least 4 hours postdose. Subjects were allowed to drink water as desired except 1 hour before and 2 hours after drug administration.

Administration under fed conditions was administration with 240 mL of water at approximately 6:00 AM, after a high-fat/high=-calorie breakfast, which included one cup of milk. Subjects began the recommended meal 30 minutes prior to drug administration. Subjects finished eating the meal in 30 minutes or less and the drug was administered approximately 30 minutes after the start of the meal. Subjects were not allowed to eat any food for at least 4 hours postdose. Subjects were allowed to drink water as desired except 1 hour before and 2 hours after drug administration.

25 Subjects completed both periods of the study. Administration of tasimelteon with a high-fat/high-calorie meal resulted in a lower $C_{max}$ and longer $T_{max}$. The mean $C_{max}$ of 786+/−432 ng/mL under fasted conditions was reduced to a mean $C_{max}$ of 445+/−255 ng/mL with a geometric mean ratio of 55.82% and an associated 90% confidence interval of 49.72% to 62.67%. The extent of absorption, as measured by $AUC_{(0-t)}$ and $AUC_{(Inf)}$ was comparable under both fed and fasted conditions with geometric mean ratios of 108.57% and 106.54%, respectively, and 90% confidence intervals contained within the 80% to 125% equivalence window. Consistent with a decrease in $C_{max}$ and no change in AUC, i.e., a decrease in the rate but not the extent of absorption, the median $T_{max}$ increased from 0.75 hours under fasted conditions to 2.5 hours under fed conditions.

From this study, it was concluded that administration of tasimelteon with a high-fat/high calorie meal results in a significant decrease in the rate of absorption but no significant change in the extent of absorption.

Thus, in illustrative embodiments, the invention comprises:

a method for administering tasimelteon to a human patient that comprises orally administering an effective dose of tasimelteon under fasted conditions;

a method for administering tasimelteon to a human patient that comprises instructing the patient that tasimelteon should be taken without food;

a method for shortening $T_{max}$ in a human patient being treated with tasimelteon, said method comprising orally administering an effective dose of tasimelteon under fasted conditions;

a method of marketing or selling tasimelteon that comprises informing prescribers, patients, and/or insurers that tasimelteon should be taken under fasted conditions, such as by including such instructions in printed prescribing information that is packaged with a container comprising tasimelteon capsules.

In specific illustrative embodiments, the fasted conditions comprises administering the tasimelteon without food;

the fasted conditions comprises no food at least ½ hour prior to administration;

the fasted conditions comprises no food at least 1 hour prior to administration;

the fasted conditions comprises no food at least 1½ hours prior to administration;

the fasted conditions comprises no food at least 2 hours prior to administration;

the fasted conditions comprises no food at least 2½ hours prior to administration; or the fasted conditions comprises no food at least 3 hours prior to administration;

In other illustrative embodiments, the $C_{max}$ is lowered while AUC is approximately the same whether the drug is administered under fed conditions or under fasted conditions;

the dose of tasimelteon is 20 mg/d;

the patient is being treated for a circadian rhythm disorder or for a sleep disorder; and/or the patient is being treated for Non-24 Disorder.

Specific illustrative language for inclusion in the prescribing information (i.e., the "label") might include, e.g.:

"The peak concentration ($T_{max}$) of tasimelteon occurred at approximately 0.5 to 3 hours after fasted oral administration. When administered with a high-fat meal, the $C_{max}$ of tasimelteon was 44% lower than when given in a fasted state, and the median $T_{max}$ was delayed by approximately 1.75 hours. Therefore, HETLIOZ should be taken without food."

What is claimed is:

1. A method of avoiding a delayed $T_{max}$, a decreased $C_{max}$, or both, resulting from the failure to administer tasimelteon without food to a patient suffering from a circadian rhythm disorder or a sleep disorder, the method comprising orally administering to the patient an effective dose of tasimelteon without food, wherein the effective dose is 20 mg/d.

2. The method of claim 1, further comprising instructing the patient that tasimelteon should be taken without food.

3. The method of claim 1, wherein the patient is suffering from a circadian rhythm disorder.

4. The method of claim 3, wherein the circadian rhythm disorder is Non-24 Disorder.

5. The method of claim 1, wherein the tasimelteon is administered with no food after at least one-half hour prior to administration.

6. The method of claim 1, wherein the tasimelteon is administered with no food after at least one hour prior to administration.

7. The method of claim 1, wherein the tasimelteon is administered with no food after at least one-and-one-half hours prior to administration.

8. The method of claim 1, wherein the tasimelteon is administered with no food after at least two hours prior to administration.

9. The method of claim 1, wherein the tasimelteon is administered with no food after at least two-and-one-half hours prior to administration.

10. The method of claim 1, wherein the tasimelteon is administered with no food after at least three hours prior to administration.

* * * * *